United States Patent
Yanagawa et al.

(10) Patent No.: US 9,844,686 B2
(45) Date of Patent: Dec. 19, 2017

(54) APPARATUS, METHOD, AND PROGRAM FOR MOVABLE PART TRACKING AND TREATMENT

(71) Applicant: KABUSHIKI KAISHA TOSHIBA, Minato-Ku (JP)

(72) Inventors: Koki Yanagawa, Tokorozawa (JP); Shinya Fukushima, Fuchu (JP); Kazunao Maeda, Nakano (JP); Keiko Okaya, Setagaya (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 145 days.

(21) Appl. No.: 14/974,395

(22) Filed: Dec. 18, 2015

(65) Prior Publication Data
US 2016/0175615 A1 Jun. 23, 2016

(30) Foreign Application Priority Data

Dec. 18, 2014 (JP) ................................ 2014-256543

(51) Int. Cl.
*G06T 7/00* (2017.01)
*A61N 5/10* (2006.01)
*G06T 7/246* (2017.01)

(52) U.S. Cl.
CPC ......... *A61N 5/1049* (2013.01); *A61N 5/1067* (2013.01); *G06T 7/248* (2017.01);
(Continued)

(58) Field of Classification Search
CPC ............... A61N 5/1049; A61N 5/1067; A61N 2005/1061; G06T 7/248; G06T 2207/10081; G06T 2207/30061
(Continued)

(56) References Cited

U.S. PATENT DOCUMENTS

2007/0182731 A1* 8/2007 Gundel ................. G06T 7/0012
345/419
2012/0223247 A1* 9/2012 Honda ................. A61N 5/1043
250/396 R

FOREIGN PATENT DOCUMENTS

| JP | 2010-194053 | 9/2010 |
| JP | 2013-78479 | 5/2013 |
| JP | 2015-66275 | 4/2015 |

* cited by examiner

Primary Examiner — Amandeep Saini
(74) Attorney, Agent, or Firm — Oblon, McClelland, Maier & Neustadt, L.L.P.

(57) ABSTRACT

According to one embodiment, A movable part tracking and treatment apparatus, includes: an acquisition unit adapted to acquire a three-dimensional moving image by imaging an inside of a body of a patient; a first projection image generation unit adapted to generate a first projection moving image by projecting the three-dimensional moving image on a two-dimensional surface from a fixed direction, the three-dimensional moving image including a tracing target and an affected part area that are part of internal organs in a displaced state, an affected part image extraction unit adapted to extract the displaced affected part area from the first projection moving image, a tracing target image extraction unit adapted to extract the displaced tracing target from the first projection moving image, a first parameter derivation unit is adapted to derive a first parameter indicative of position information on a beam irradiation point selected from the displaced affected part area in the first projection moving image, and a second parameter derivation unit adapted to derive a second parameter necessary to extract the corresponding tracing target from another projection moving image based on the tracing target extracted from the first projection moving image.

11 Claims, 6 Drawing Sheets

(52) U.S. Cl.
CPC ............... *A61N 2005/1061* (2013.01); *G06T 2207/10081* (2013.01); *G06T 2207/30061* (2013.01)

(58) Field of Classification Search
USPC ................................................ 382/103, 131
See application file for complete search history.

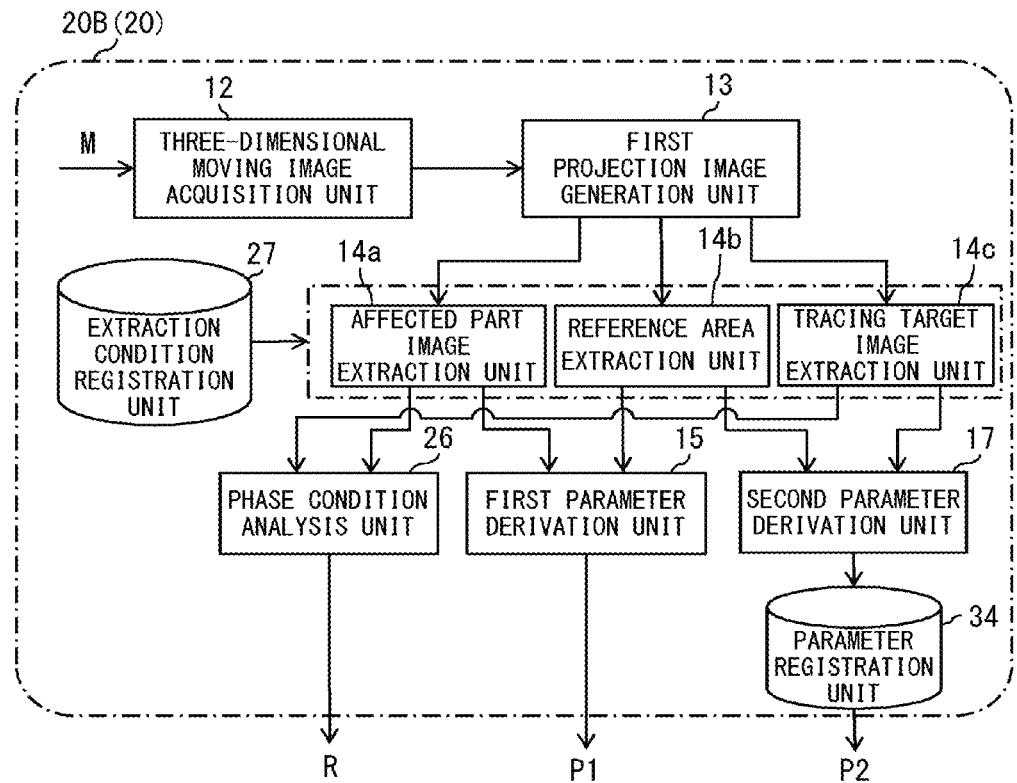

FIG. 7

| AFFECTED PART AREA | TRACING TARGET | EXTRACTION CONDITION | COMBINATION | PERMISSION/NON-PERMISSION | IMAGE PROCESSING 1 | IMAGE PROCESSING 2 | IMAGE PROCESSING 3 | STORAGE |
|---|---|---|---|---|---|---|---|---|
| 52b | 51b | EDGE 1> THRESHOLD | 3 | PERMIT | NOISE REMOVAL 1 | EDGE DETECTION 1 | THINNING | NOT STORED |
| 52b | 51p | EDGE 2> THRESHOLD | 3 | PERMIT | NOISE REMOVAL 2 | EDGE DETECTION 2 | | STORED |
| 52b | 51q | LABEL 1> THRESHOLD | 3 | PERMIT | NOISE REMOVAL 3 | LABEL DETECTION 1 | | STORED |
| 52b | 51r | PATTERN 1 | | NOT PERMITTED | NOISE REMOVAL 4 | TEMPLATE | | NOT STORED |

FIG. 8

APPARATUS, METHOD, AND PROGRAM FOR MOVABLE PART TRACKING AND TREATMENT

CROSS-REFERENCE TO RELATED APPLICATIONS

This application is based upon and claims the benefit of priority from Japanese Patient application No. 2014-256543, filed on Dec. 18, 2014, the entire contents of each of which are incorporated herein by reference.

BACKGROUND OF THE INVENTION

Field of the Invention

Embodiments of the present invention relate to a movable part tracking and treatment technique for treating an affected part of a patient displaced by respiration and other factors by emission of a beam.

Description of the Related Art

As a treatment technique for malignant tumors such as cancer, a technique using particle beams is attracting attention because of its excellent features such as high therapeutic effects, low side effects, and reduced load to the body.

When a particle beam enters a body of a patient, the beam loses its kinetic energy in the process of passing the body. Once the beam slows down to a certain prescribed rate, it suddenly stops and generates a large dose of radiation called a Bragg peak.

With the large dose of radiation generated at a pinpoint in this way, only cancer cells can be shot and killed while influence on healthy cells can be minimized.

Therefore, treatment apparatuses using a particle beam are required to accurately aim the beam to be emitted to the affected part so as to prevent normal tissues from being damaged.

Accordingly, in advance of emitting the beam, a position of the affected part is specified by X-ray observation and the like, and a position and an angle of a movable bed with the patient mounted thereon are appropriately adjusted, so that the affected part is accurately positioned within an emission range of the beam.

When the beam is emitted to an affected part present in an internal organ with motion (lung and the like), it is necessary to determine emission timing in consideration of periodic displacement caused by respiration and the like to ensure the accuracy of beam emission.

In such a case, a method as described below is conventionally adopted. That is, a gold marker or the like is embedded in a vicinity of an affected part, or the marker is pasted on a body surface of the patient, and movement of the marker is tracked with the aid of X-ray photography to identify the position of the affected part.

Patent Document 1

Japanese Patent Laid-Open No. 2014-54302

Patent Document 2

Japanese Patent Laid-Open No. 2013-78479

Patent Document 3

Japanese Patent Laid-Open No. 2000-167072

However, the method for embedding the marker in the vicinity of the affected part increases a load of the patient since the method involves a costly process of manufacturing exclusive markers as well as surgical operation.

The method for pasting the marker on the body surface of the patient poses a less burden on the patient, but has more limitations in terms of practical application, such as the necessity of separately provided special detecting cameras and synchronizers and fine position adjustment of these devices.

SUMMARY OF THE INVENTION

Embodiments of the present invention have been made in consideration of such circumstances, and it is therefore an object of the embodiments to provide a movable part tracking and treatment technique capable of accurately tracking an affected part which is being displaced without using a marker.

A movable part tracking and treatment apparatus according to an embodiment of the present invention, including: an acquisition unit; a first projection image generation unit; an affected part image extraction unit; a tracing target image extraction unit; a first parameter derivation unit; a second parameter derivation unit; a determination unit; a tracing target identification unit; a phase determination unit; and a beam emission unit. In the apparatus, the acquisition unit is adapted to acquire a three-dimensional moving image by imaging an inside of a body of a patient. The first projection image generation unit is adapted to generate a first projection moving image by projecting the three-dimensional moving image on a two-dimensional surface from a fixed direction, the three-dimensional moving image including a tracing target and an affected part area that are part of internal organs in a displaced state. The affected part image extraction unit is adapted to extract the displaced affected part area from the first projection moving image. The tracing target image extraction unit is adapted to extract the displaced tracing target from the first projection moving image. The first parameter derivation unit is adapted to derive a first parameter indicative of position information on a beam irradiation point selected from the affected part area displaced in the first projection moving image. The second parameter derivation unit is adapted to derive a second parameter necessary to extract the corresponding tracing target from another projection moving image based on the tracing target extracted from the first projection moving image. The determination unit is adapted to determine position information on a treatment table at least based on the first parameter, the treatment table having the patient mounted thereon and being moved for aiming the beam. The tracing target identification unit is adapted to identify, based on the second parameter, the tracing target from the second projection moving image of the patient imaged after the treatment table is moved based on the position information. The phase determination unit is adapted to monitor a phase of the tracing target displaced in the second projection moving image and to determine whether or not the phase satisfies a phase condition whereby the affected part area is displaced and matches with the irradiation point. The beam emission unit is adapted to emit the beam at a timing when it is determined that the phase condition is satisfied.

The embodiments of the present invention can provide a movable part tracking and treatment technique that can accurately track a displaced affected part without using a marker.

BRIEF DESCRIPTION OF THE DRAWINGS

FIG. 7 is a block diagram illustrating a movable part tracking and treatment apparatus according to a third embodiment of the present invention; and FIG. 8 is a table of extraction conditions classified in accordance with types of tracing targets or affected part areas used for extracting a tracing target or an affected part area from the first projection moving image.

DETAILED DESCRIPTION OF THE PREFERRED EMBODIMENTS

Embodiments of the present invention will be described hereinbelow with reference to accompanying drawings.

First Embodiment

Figure 1:
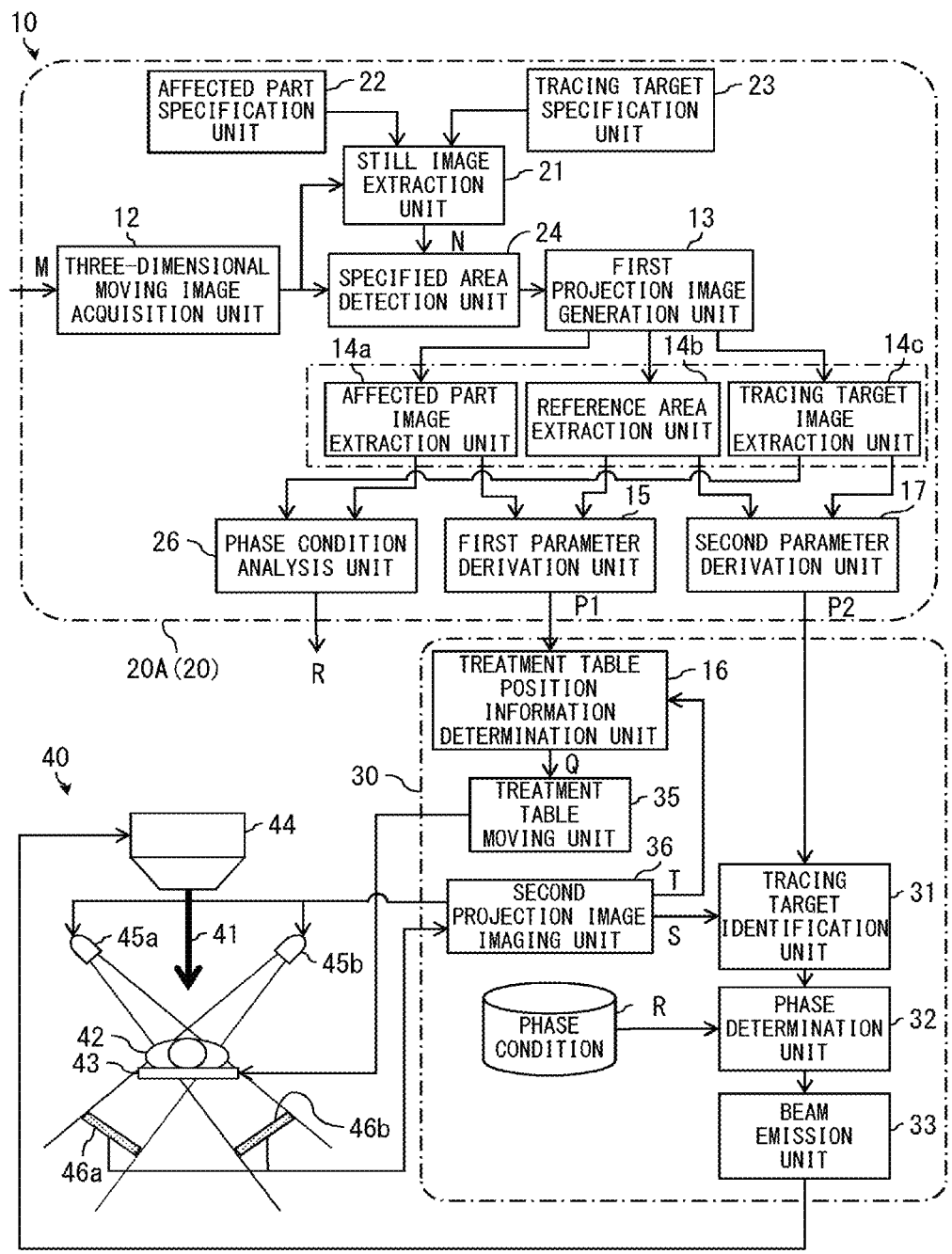
FIG. 1 is a block diagram illustrating a movable part tracking and treatment apparatus according to a first embodiment of the present invention.
Figure 2:
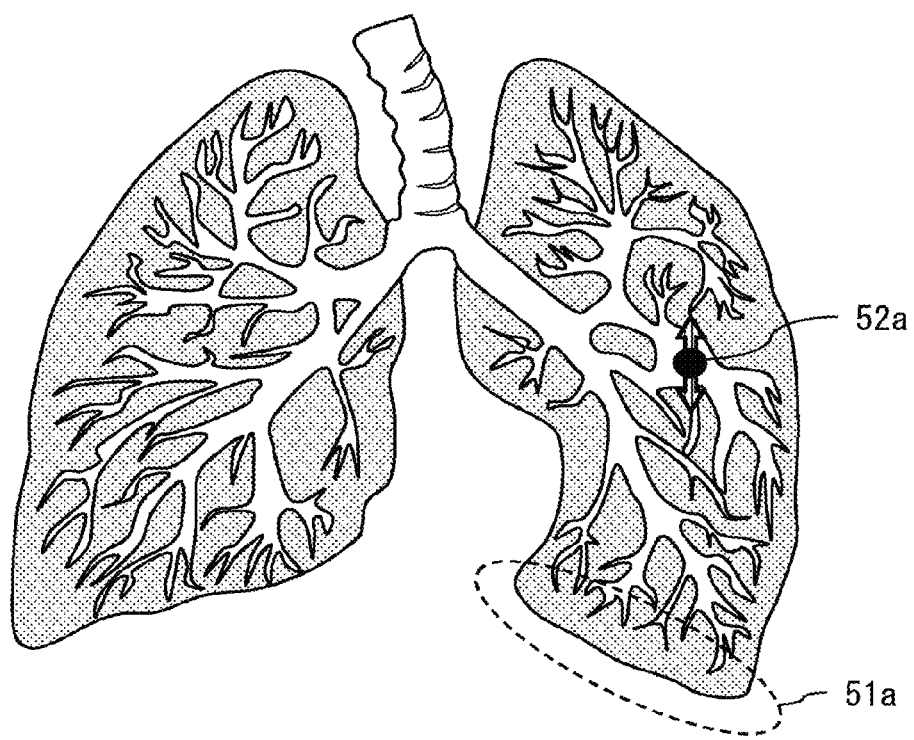
FIG. 2 illustrates a first projection moving image obtained by projecting a three-dimensional moving image of a patient's lung on a two-dimensional surface.

As illustrated in FIG. 1, a movable part tracking and treatment apparatus 10 according to a first embodiment includes: an acquisition unit 12; a first projection image generation unit 13; an affected part image extraction unit 14a; a tracing target image extraction unit 14c; a first parameter derivation unit 15; a second parameter derivation unit 17; a determination unit 16; a tracing target identification unit 31; a phase determination unit 32; and a beam emission unit 33. The acquisition unit 12 is adapted to acquire a three-dimensional moving image M by imaging an inside of a body of a patient. The first projection image generation unit 13 is adapted to generate a first projection moving image (FIG. 2) by projecting the three-dimensional moving image M on a two-dimensional surface from a fixed direction, the three-dimensional moving image M including a tracing target 51a (see FIG. 2) and an affected part area 52a that are part of internal organs in a displaced state. The affected part image extraction unit 14a is adapted to extract the displaced affected part area 52a from the first projection moving image (FIG. 2). The tracing target image extraction unit 14c is adapted to extract the displaced tracing target 51a from the first projection moving image (FIG. 2). The first parameter derivation unit 15 is adapted to derive a first parameter P1 indicative of position information on a beam irradiation point G (FIG. 3) selected from the displaced affected part area 52a in the first projection moving image (FIG. 2). The second parameter derivation unit 17 is adapted to derive a second parameter P2 necessary to extract a corresponding tracing target 51b (FIG. 4) from another projection moving image based on the tracing target 51a extracted from the first projection moving image (FIG. 2). The determination unit 16 is adapted to determine position information Q on a treatment table 43 at least based on the first parameter P1, the treatment table 43 having the patient 42 mounted thereon and being moved for aiming the beam 41. The tracing target identification unit 31 is adapted to identify, based on the second parameter P2, the tracing target 51b from the second projection moving image S (FIG. 4) of the patient 42 imaged after the treatment table 43 is moved based on the position information Q. The phase determination unit 32 is adapted to determine whether or not a phase of the tracing target 51b displaced in the second projection moving image S satisfies a phase condition R whereby the affected part area 52b is displaced and matches with the irradiation point G. The beam emission unit 33 is adapted to emit the beam 41 at a timing when the phase condition R is satisfied.

The movable part tracking and treatment apparatus 10 further includes: an extraction unit 21, an affected part specification unit 22, a tracing target specification unit 23, and a specified area detection unit 24. The extraction unit 21 is adapted to extract a three-dimensional still image N from the three-dimensional moving image M. The affected part specification unit 22 is adapted to specify the affected part area (illustration omitted) included in the three-dimensional still image N. The tracing target specification unit 23 is adapted to specify the tracing target (illustration omitted) included in the three-dimensional still image N. The specified area detection unit 24 is adapted to detect the affected part area (illustration omitted) and the displaced tracing target (illustration omitted) displaced in the three-dimensional moving image M based on the affected part area and the tracing target specified in the three-dimensional still image N.

The movable part tracking and treatment apparatus 10 according to the embodiment includes: a treatment apparatus main body 40, a control unit 30 of the treatment apparatus main body 40, and a control parameter regulation unit 20A (20).

In treatment using a particle beam, a step of using the movable part tracking and treatment apparatus 10 is conducted after preceding steps, such as making fixing tools, simulation, CT photographing, and rehearsal, are conducted.

In the step of CT photographing out of these preceding steps, a three-dimensional moving image M of the patient is imaged with an X-ray CT scanner and the like to derive an energy condition of the beam 41 emitted to the affected part.

The three-dimensional moving image M is sent to an acquisition unit 12 of the control parameter regulation unit 20A, where the three-dimensional moving image M is used for deriving the first parameter P1 that is one of the control parameters of the treatment table 43 necessary for aiming the beam 41 and for deriving the second parameter P2 necessary for recognizing the tracing target.

Here, a data format of the three-dimensional moving image M is not particularly specified. Any data format is usable as long as the position of the ever-changing affected part area 52a can be identified with respect to a time-axis.

Therefore, the three-dimensional moving image M may be an assembly of a plurality of three-dimensional still images obtained by time-dividing single-period data on the affected part area 52a depicting a closed loop track.

The still image extraction unit 21 extracts one three-dimensional still image N taken at any one time from the three-dimensional moving image M. The still image extraction unit 21 plays a role of accurately identifying contours of the tracing target and the affected part area, which are being displaced, in a still state.

An operator operates the affected part specification unit 22 and the tracing target specification unit 23 to specify the affected part area (illustration omitted) and the tracing target (illustration omitted) which are included in the three-dimensional still image N.

Here, the tracing target to be specified needs to have respiration-induced repetitive displacement which is in conjunction with replacement of the affected part area.

Specifically, in the case of treating an affected part inside the lung, a diaphragm may be specified as a tracing target. The tracing target may also be specified by applying such image extraction methods as edge detection, contour detection, and template matching.

The specified area detection unit 24 is adapted to detect the affected part area (illustration omitted) and the displaced tracing target (illustration omitted) displaced in the three-dimensional moving image M based on the affected part area and the tracing target specified in the three-dimensional still image N. This makes it possible to accurately grasp relevancy between displacement of the affected part area and displacement of the tracing target in three dimensional space.

The first projection image generation unit 13 projects a three-dimensional moving image M on a two-dimensional surface from a fixed direction to generate a first projection moving image illustrated in FIG. 2. Thus, according to the first projection moving image (FIG. 2), the tracing target 51a and the affected part area 52a in a displaced state can be grasped on the two-dimensional surface.

The first projection moving image (FIG. 2) is projected in a direction similar to a direction of a second projection moving image S (FIG. 4) described later.

The affected part image extraction unit 14a extracts the affected part area 52a displaced in the first projection moving image (FIG. 2). That is, the affected part area 52a corresponds to an affected part area which is detected in the specified area detection unit 24 and projected on the two-dimensional surface from three dimensional space.

The reference area extraction unit 14b extracts an area without displacement in the first projection moving image (FIG. 2) as a reference area. Specifically, the contours of a backbone, organs, and the like, which are not displaced by respiration, are selected. The reference area serves as a reference at the time of aiming the beam at the later-described treatment table 43. When objects other than the body of the patient 42, such as the treatment table 43 with the patient 42 mounted thereon, are used as a reference, the reference area extraction unit 14b may be omitted.

The tracing target image extraction unit 14c extracts the tracing target 51a displaced in the first projection moving image (FIG. 2). That is, the tracing target 51a corresponds to a tracing target which is detected in the specified area detection unit 24 and projected on the two-dimensional surface from three dimensional space.

Figure 3:
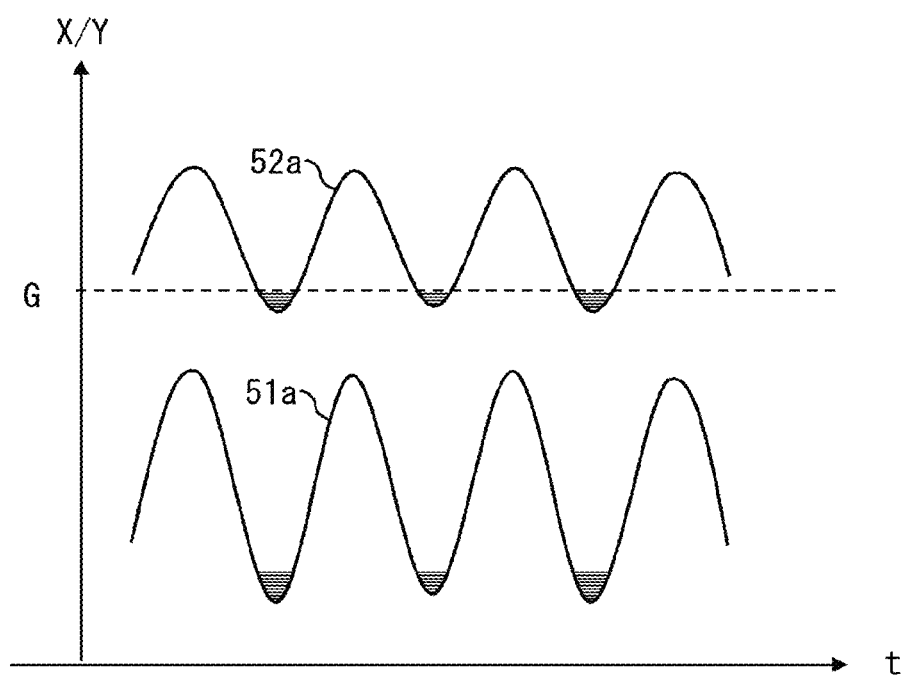
FIG. 3 is a graph view illustrating tracks of a tracing target and an affected part displaced by respiration.
Figure 4:
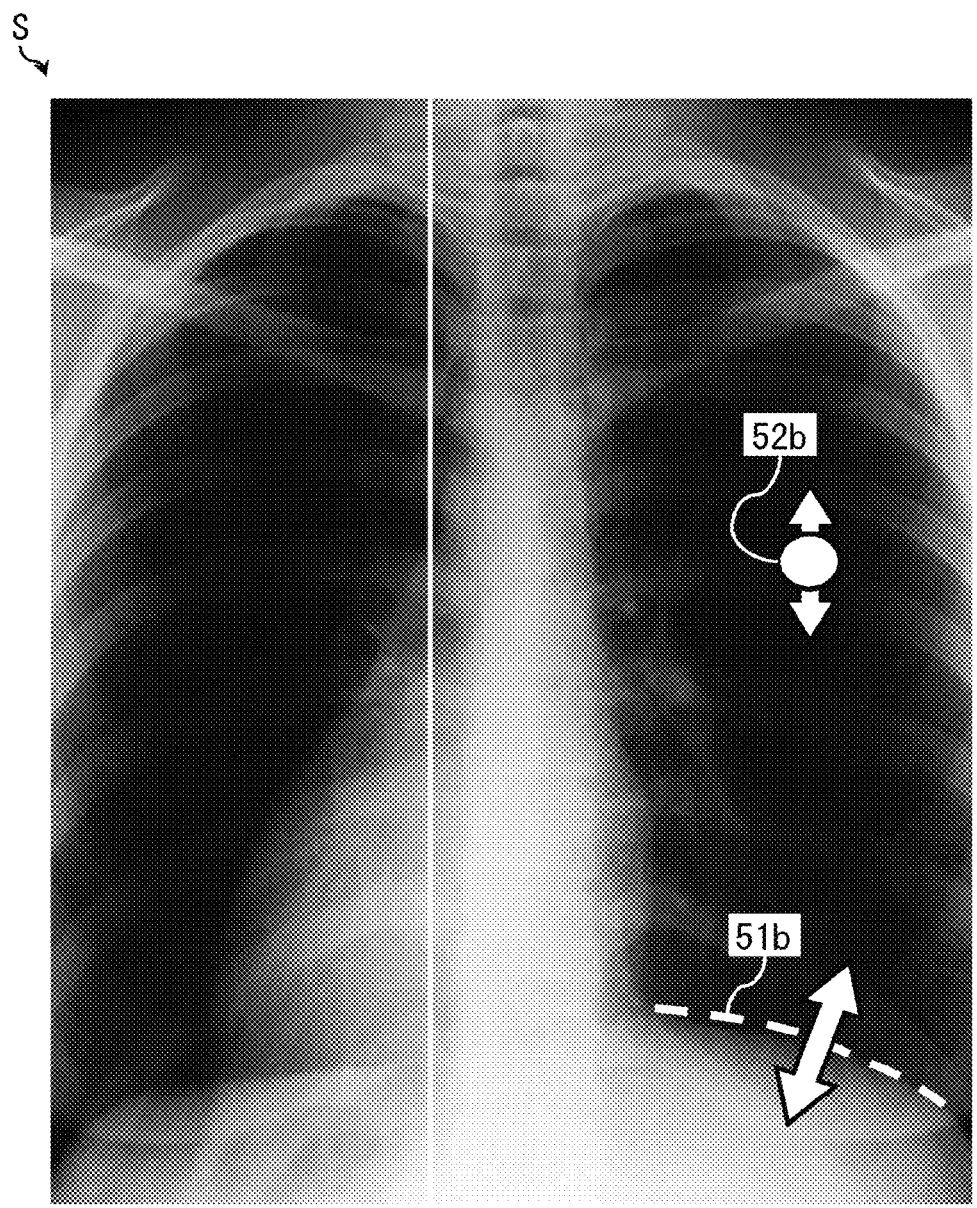
FIG. 4 illustrates a second projection moving image obtained by imaging the patient mounted on a treatment table.

FIG. 3 is a graph view illustrating tracks of respiration-induced displacement of Y component (or X component) of the tracing target 51a and the affected part area 52a with respect to the time axis, wherein X and Y are fixed coordinates set in a reference area in the first projection moving image (FIG. 2).

As illustrated in the graph view, the displacement of the tracing target 51a is in synchronization with the displacement of the affected part area 52a, and therefore the point G of the affected part area 52a irradiated with the beam 41 (FIG. 1) can be calculated based on a displacement phase of the tracing target 51a.

In FIG. 3, the irradiation point G is set at a position where the affected part area 52a has a minimum displacement value. However, the irradiation point G is not limited thereto. An arbitrary position can be selected as the irradiation point G.

The phase condition analysis unit 26 compares the tracks of the tracing target 51a and the affected part area 52a to analyze the phase condition R of the tracing target 51a at a timing when the position of the affected part area 52a matches with the irradiation point G.

Accordingly, the tracing target 51a is tracked, and the beam 41 is aimed at the irradiation point G of the affected part area 52a at the timing when the phase condition R is satisfied.

Thus, the first parameter derivation unit 15 selects the irradiation point G to be irradiated with the beam 41 from the displaced affected part area 52a, and derives the first parameter P1 indicative of the position information on the irradiation point G. The first parameter P1 is set by a coordinate system using an unmovable area such as the backbone in the first projection moving image (FIG. 2) as a reference area.

The second parameter derivation unit 17 derives the second parameter P2 necessary to extract the corresponding tracing target 51b from another projection moving image (for example, a second projection moving image S (FIG. 4)) based on the tracing target 51a extracted from the first projection moving image (FIG. 2).

More specifically, the second parameter P2 identifies an object area displaced inside the two-dimensional image, based on schematic position information, schematic shape information, and schematic track information in the two-dimensional image.

The treatment table position information determination unit 16 determines the position information Q indicative of the position of the treatment table 43 in the treatment apparatus main body 40 so that a beam irradiation port 44 faces in a direction crossing the irradiation point G of the patient 42. The position information Q can be determined based on the first parameter P1 if a coordinate system based on the reference area (backbone and the like) inside the first projection moving image (FIG. 2) is correlated with a coordinate system of the moving unit 35 that moves the treatment table 43.

Specifically, the projection still image T of the patient 42 is imaged by two pairs of X-ray irradiation units 45 (45a, 45b) and X-ray detection units 46 (46a, 46b) provided in the treatment apparatus main body 40. By extracting the corresponding reference area (backbone and the like) from the projection still image T, the coordinate system of the reference area (backbone and the like) can be incorporated into the coordinate system of the moving unit 35.

More specifically, the treatment table 43 with the patient 42 mounted thereon is moved and temporarily positioned. Then, the second projection image imaging unit 36 images a projection still image T. The projection still image T is then sent to the treatment table position information determination unit 16, where the position information Q on the treatment table 43 is determined based on the first parameter P1.

When objects other than the body of the patient 42, such as the treatment table 43, are used as a reference, imaging of the projection still image T may be omitted.

The treatment table moving unit 35 moves the treatment table 43 based on the position information Q for aiming the beam 41 at the irradiation point G of the patient 42 mounted thereon.

After the treatment table 43 is moved based on the position information Q, the projection still image T may be imaged again to derive a deviation amount from the position of the reference area (backbone and the like), and the treatment table 43 may be moved again for position adjustment as necessary.

Thus, in the treatment apparatus main body 40, after the position of the treatment table 43 is fixed with the patient 42 mounted thereon, the second projection image imaging unit 36 is operated to start imaging of a second projection moving image S without operating the treatment table moving unit 35.

The tracing target identification unit 31 acquires the second parameter P2 to identify the tracing target 51b from the second projection moving image S currently being imaged, and monitors the track of the tracing target.

Since the second projection moving image S (FIG. 4) is lower in resolution than the first projection moving image (FIG. 2), the affected part area 52b cannot sufficiently be identified.

The phase determination unit 32 determines whether or not the phase of the tracing target 51b displaced in the second projection moving image S satisfies the phase condition R.

If the phase of the tracing target 51b satisfies the phase condition R, the beam 41 is focused on the irradiation point G of the affected part area 52b, which is difficult to identify in the second projection moving image S.

The beam emission unit 33 emits the beam 41 at the timing when the phase of the monitored tracing target 51b is determined to satisfy the phase condition R.

The emitted beam 41 generates a Bragg peak at the position of the affected part area 52b displaced to the irradiation point G and thereby kills cells existing in the affected part area 52b.

Figure 5:
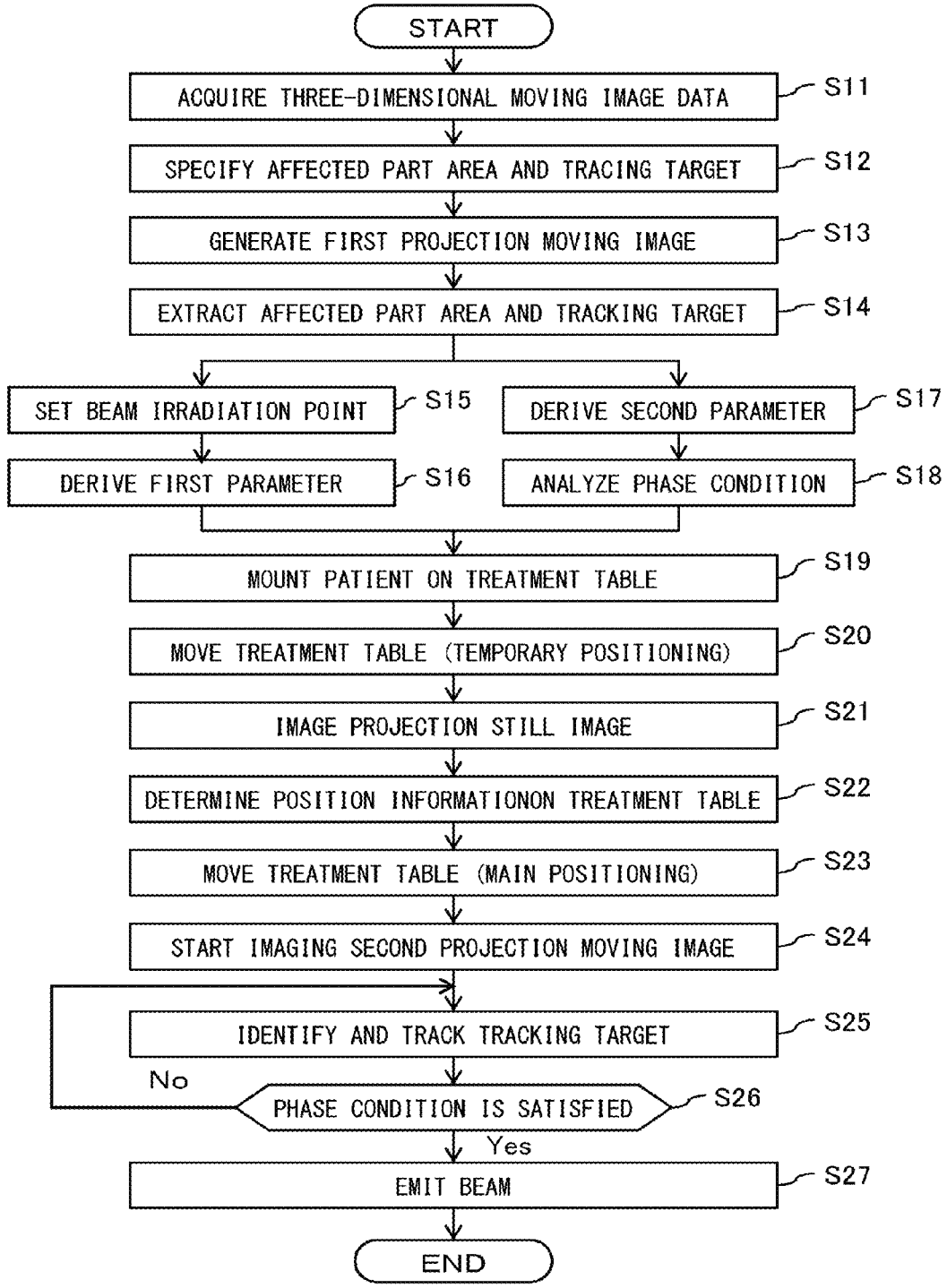
FIG. 5 is a flowchart illustrating a method or program for movable part tracking and treatment according to the embodiments of the present invention.

A method and a program for movable part tracking and treatment according to the embodiment will be described with reference to a flowchart of FIG. 5.

A three-dimensional moving image is acquired by imaging the inside of the body of the patient with an X-ray CT scanner and the like (S11), and an affected part area and a tracing target are specified from the three-dimensional moving image (S12).

The three-dimensional moving image in the state where the displaced tracing target and affected part area are identified is projected on a two-dimensional surface from a fixed direction to generate a first projection moving image (FIG. 2) (S13).

The displaced affected part area 52a and tracing target 51a are extracted from this first projection moving image (FIG. 2) (S14).

An irradiation point irradiated with the beam is set in the extracted affected part area 52a (S15), and the first parameter P1 indicative of position information on the irradiation point is derived (S16).

Meanwhile, the second parameter necessary to extract a corresponding tracing target 51b from the second projection moving image S imaged later is derived based on the extracted tracing target 51a (S17).

Furthermore, a phase condition of the tracing target 51a at the timing when the affected part area 52a matches with the irradiation point is analyzed (S18).

After the patient 42 is mounted on the treatment table 43 (S19), the treatment table 43 is moved to directly under the beam irradiation port 44 and is temporarily positioned (S20). Then, the projection still image T of the patient 42 is imaged (S21), and the position information Q on the treatment table, which is used for aiming the beam 41 at the irradiation point of the patient 42, is determined based on the projection still image T and the first parameter P1 (S22).

The treatment table 43 is then moved based on this position information Q, and main positioning is performed (S23).

The second projection moving image S of the patient 42 mounted on the treatment table 43 starts to be imaged (S24). The tracing target 51b is identified from the second projection moving image S based on the second parameter and is tracked (S25).

Whether or not the phase of the tracing target 51b satisfies the phase condition (No/Yes in S26) is determined, and if the condition is satisfied, the beam 41 is emitted at that timing (S27).

Second Embodiment

Figure 6:
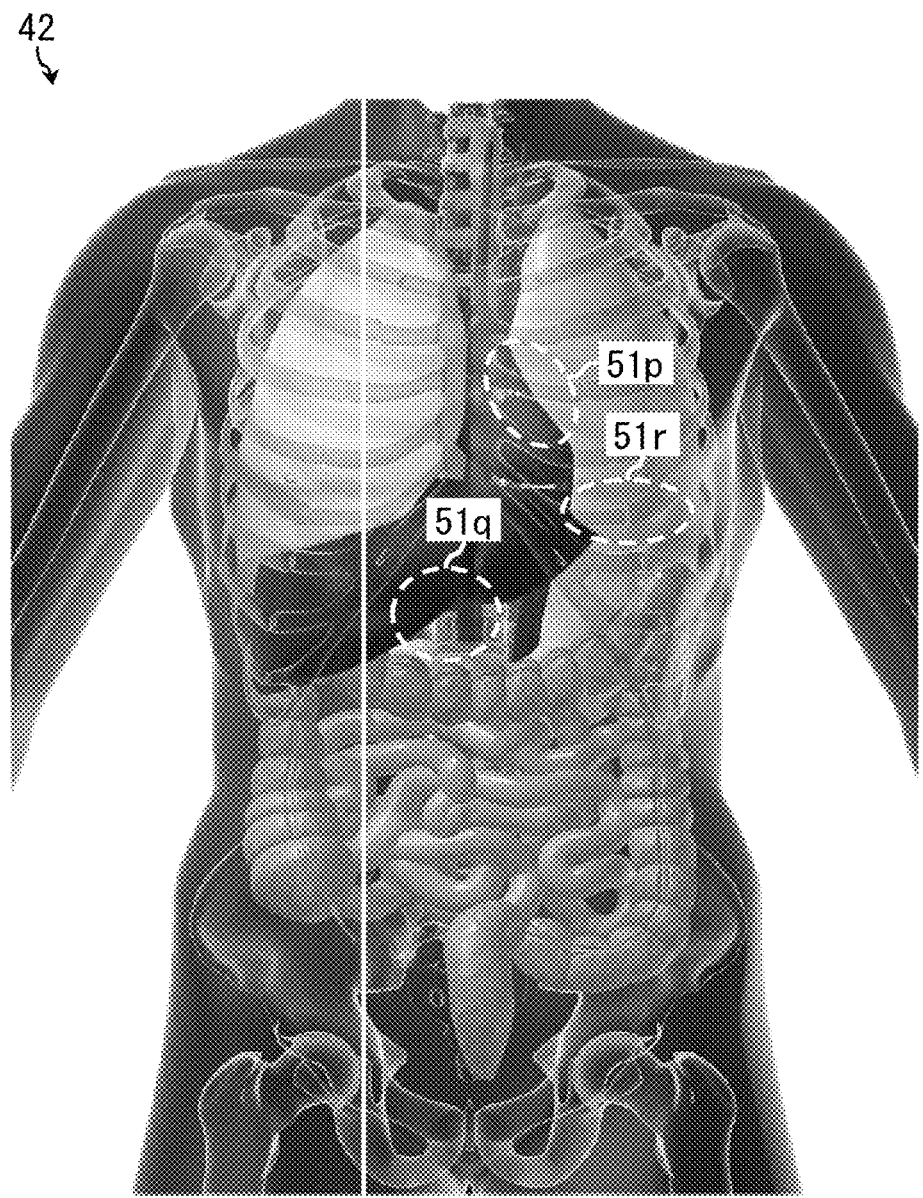
FIG. 6 illustrates candidates of the tracing target provided inside the body of the patient.

FIG. 6 illustrates candidates of the tracing target 51 (51p, 51q, 51r) inside the body of the patient 42. In the first embodiment, the diaphragm is set as the tracing target 51a (FIG. 2). However, the tracing target to be selected is not particularly limited. Any portion can be selected as long as it is displaced in conjunction with the affected part area 52.

Examples of body regions moving in unison and conjunction with respiration include part of the lung (reference numeral 51p), part of a liver (reference numeral 51q), and ribs (reference numeral 51r).

Body regions to be selected as the tracing target 51 is not limited to any one of the regions, but two or more regions may be selected.

Accordingly, in the second embodiment, the tracing target specification unit 23 (FIG. 1) can set the plurality of tracing targets 51 at each of different positions inside the body of the patient 42.

The tracing target image extraction unit 14c extracts each of the plurality of tracing targets 51 (51p, 51q, 51r) included in the first projection moving image.

In the second parameter derivation unit 17, a plurality of second parameter P2 corresponding to each of the plurality of tracing targets 51 (51p, 51q, 51r) are derived.

The phase condition analysis unit 26 compares tracks of the respective tracing targets 51 (51p, 51q, 51r) and the affected part area 52a. The phase condition analysis unit 26 then analyzes the plurality of phase conditions R with respect to each of the tracing targets 51 (51p, 51q, 51r) at the timing when the position of the affected part area 52a matches with the irradiation point G.

The tracing target identification unit 31 identifies the plurality of corresponding tracing targets 51 based on the plurality of second parameters P2. The phase determination unit 32 independently monitors each phase of the plurality of identified tracing targets 51, determines whether or not the phase conditions R are satisfied for each of the tracing targets 51, and determines the timing of emitting the beam 41.

Third Embodiment

Next, a third embodiment in the present invention will be described with reference to FIG. 7. In FIG. 7, component parts common in configuration or function with those in FIG. 1 are designated by identical reference numerals and redundant description thereof will be omitted.

A movable part tracking and treatment apparatus according to the third embodiment does not include the still image extraction unit 21, the affected part specification unit 22, the tracing target specification unit 23, and the specified area detection unit 24 in the first embodiment (FIG. 1). Instead, the movable part tracking and treatment apparatus according to the third embodiment includes an extraction condition registration unit 27 in the control parameter regulation unit 20B (20), and further includes a parameter registration unit 34.

The extraction condition registration unit 27 classifies and registers conditions to extract the tracing target 51 or the affected part area 52 from the first projection moving image (FIG. 2) in accordance with the type of the tracing target or the affected part as illustrated in FIG. 8.

Which affected part area 52 to adopt can be determined by selecting a permission or non-permission check box. When the plurality of affected part areas 52 are adopted, a plurality of corresponding permission check boxes are selected.

Image processing methods can also be set. For example, when edge detection 1 is set as an extraction condition, execution of preceding processing, such as execution of noise removal 1, edge detection 1, and thinning in this order, can be set for each of the tracing targets 51 (51b, 51p, 51q, 51r).

Although not illustrated, general image processing methods such as leveling, LOG filtering, and differentiation detection can also be set for image processing of these affect part areas. In addition, specialized processing for removing and extracting specified parts of body regions may also be set.

The parameter registration unit 34 registers the second parameters P2 classified in accordance with the types of the tracing targets 51.

Thus, the second parameters P2 registered in advance can be used for treatment of other patients 42, without the necessity of extracting a new second parameter P2.

According to the movable part tracking and treatment apparatus at least in one embodiment described in the foregoing, part of internal organs is set as a tracing target. This makes it possible to accurately aim the beam emitted to the affected part area displaced by respiration and other factors, without using a marker.

Although some embodiments of the present invention have been described, these embodiments are in all respects illustrative and are not considered as the basis for restrictive interpretation of the invention. It should be understood that these embodiments can be performed in other various forms and that various removals, replacements, modifications, and combinations are possible without departing from the meaning of the invention. These embodiments and their modifications are intended to be embraced in the range and meaning of the invention and are intended to be embraced in the invention disclosed in the range of the claims and the equivalency thereof.

Component members of the movable part tracking and treatment apparatus may be implemented by a processor of a computer and be operative by a movable part tracking and treatment program.

What is claimed is:

1. A movable part tracking and treatment apparatus, comprising:
   an acquisition unit;
   a first projection image generation unit;
   an affected part image extraction unit;
   a tracing target image extraction unit;
   a first parameter derivation unit; and
   a second parameter derivation unit, wherein
   the acquisition unit is adapted to acquire a three-dimensional moving image by imaging an inside of a body of a patient;
   the first projection image generation unit is adapted to generate a first projection moving image by projecting the three-dimensional moving image on a two-dimensional surface from a fixed direction, the three-dimensional moving image including a tracing target and an affected part area that are part of internal organs in a displaced state,
   the affected part image extraction unit is adapted to extract the displaced affected part area from the first projection moving image,
   the tracing target image extraction unit is adapted to extract the displaced tracing target from the first projection moving image,
   the first parameter derivation unit is adapted to derive a first parameter indicative of position information on a beam irradiation point selected from the displaced affected part area in the first projection moving image, and
   the second parameter derivation unit is adapted to derive a second parameter necessary to extract the corresponding tracing target from another projection moving image based on the tracing target extracted from the first projection moving image.

2. The movable part tracking and treatment apparatus according to claim 1, further comprising:
   a determination unit;
   a tracing target identification unit;
   a phase determination unit; and
   a beam emission unit, wherein
   the determination unit is adapted to determine position information on a treatment table at least based on the first parameter, the treatment table having the patient mounted thereon and being moved for aiming the beam;
   the tracing target identification unit is adapted to identify, based on the second parameter, the tracing target from the second projection moving image of the patient imaged after the treatment table is moved based on the position information,
   the phase determination unit is adapted to determine whether or not a phase of the tracing target displaced in the second projection moving image satisfies a phase condition whereby the affected part area is displaced and matches with the irradiation point, and
   the beam emission unit is adapted to emit the beam at a timing when it is determined that the phase condition is satisfied.

3. The movable part tracking and treatment apparatus according to claim 1, further comprising:
   an extraction unit;
   an affected part specification unit;
   a tracing target specification unit; and
   a specified area detection unit, wherein
   the extraction unit is adapted to extract a three-dimensional still image from the three-dimensional moving image,
   the affected part specification unit is adapted to specify the affected part area included in the three-dimensional still image,
   the tracing target specification unit is adapted to specify the tracing target included in the three-dimensional still image, and
   the specified area detection unit is adapted to detect the affected part area and the tracing target displaced in the three-dimensional moving image based on the affected part area and the tracing target specified in the three-dimensional still image.

4. The movable part tracking and treatment apparatus according to claim 1, wherein a plurality of tracing targets are set at each of different positions inside the body of the patient, a plurality of second parameters corresponding to each of the plurality of tracing targets are derived, and phases of the plurality of tracing targets identified based on the plurality of second parameters are each independently monitored, and whether or not a phase condition is satisfied is determined for each of the tracing targets to determine timing of emitting the beam.

5. The movable part tracking and treatment apparatus according to claim 1, further comprising
a registration unit adapted to register the second parameter classified in accordance with a type of the tracing target.

6. The movable part tracking and treatment apparatus according to claim 1, further comprising
an analysis unit adapted to compare displacement of the affected part area and displacement of the tracing target extracted from the first projection moving image to analyze a phase condition of the tracing target used as timing to emit the beam.

7. The movable part tracking and treatment apparatus according to any one of claim 1, further comprising
a registration unit adapted to classify and register conditions to extract the tracing target or the affected part area from the first projection moving image in accordance with a type of the tracing target or the affected part area.

8. A method for movable part tracking and treatment, comprising:
an acquisition step;
a first projection moving image generation step;
an affected part area extraction step;
a tracing target extraction step;
a first parameter derivation step; and
a second parameter derivation step, wherein
the acquisition step is to acquire a three-dimensional moving image by imaging an inside of a body of a patient,
the first projection moving image generation step is to generate a first projection moving image by projecting the three-dimensional moving image on a two-dimensional surface from a fixed direction, the three-dimensional moving image including a tracing target and an affected part area that are part of internal organs in a displaced state,
the affected part area extraction step is to extract the displaced affected part area from the first projection moving image,
the tracing target extraction step is to extract the displaced tracing target from the first projection moving image,
the first parameter derivation step is to derive a first parameter indicative of position information on a beam irradiation point selected from the affected part area displaced in the first projection moving image, and
the second parameter derivation step is to derive a second parameter necessary to extract the corresponding tracing target from another projection moving image based on the tracing target extracted from the first projection moving image.

9. The method for movable part tracking and treatment according to claim 8, further comprising:
a determination step;
a tracing target identification step;
a phase determination step; and
a beam emission step, wherein the determination step is to determine position information on a treatment table at least based on the first parameter, the treatment table having the patient mounted thereon and being moved for aiming the beam;
the tracing target identification step is to identify, based on the second parameter, the tracing target from the second projection moving image of the patient imaged after the treatment table is moved based on the position information,
the phase determination step is to determine whether or not a phase of the tracing target displaced in the second projection moving image satisfies a phase condition whereby the affected part area is displaced and matches with the irradiation point, and
the beam emission step is to emit the beam at a timing when it is determined that the phase condition is satisfied.

10. A movable part tracking and treatment program for causing a computer to execute the steps comprising:
an acquisition step;
a first projection moving image generation step;
an affected part area extraction step;
a tracing target extraction step;
a first parameter derivation step; and
a second parameter derivation step, wherein
the acquisition step is to acquire a three-dimensional moving image by imaging an inside of a body of a patient,
a first projection moving image generation step is to generate a first projection moving image by projecting the three-dimensional moving image on a two-dimensional surface from a fixed direction, the three-dimensional moving image including a tracing target and an affected part area that are part of internal organs in a displaced state,
the affected part area extraction step is to extract the displaced affected part area from the first projection moving image,
the tracing target extraction step is to extract the displaced tracing target from the first projection moving image,
the first parameter derivation step is to derive a first parameter indicative of position information on a beam irradiation point selected from the affected part area displaced in the first projection moving image, and
the second parameter derivation step is to derive a second parameter necessary to extract the corresponding tracing target from another projection moving image based on the tracing target extracted from the first projection moving image.

11. The movable part tracking and treatment program according to claim 10 for causing a computer to further execute the steps comprising:
a determination step;
a tracing target identification step;
a phase determination step; and
a beam emission step, wherein
the determination step is to determine position information on a treatment table at least based on the first parameter, the treatment table having the patient mounted thereon and being moved for aiming the beam;
the tracing target identification step is to identify, based on the second parameter, the tracing target from the second projection moving image of the patient imaged after the treatment table is moved based on the position information, the phase determination step is to determine whether or not a phase of the tracing target displaced in the second projection moving image satisfies a phase condition whereby the affected part area is displaced and matches with the irradiation point, and the beam emission step is to emit the beam at a timing when it is determined that the phase condition is satisfied.

\* \* \* \* \*